United States Patent [19]

Takahashi et al.

[11] Patent Number: 5,686,055
[45] Date of Patent: Nov. 11, 1997

[54] PROCESS FOR RECOVERING PHTHALIC ANHYDRIDE AND HYDROGEN CHLORIDE FROM PLASTIC MATERIALS

[75] Inventors: Toshiki Takahashi, Higashihiroshima; Tatsuto Fukushima, Hiroshima-ken; Yoshio Tanimoto, Hiroshima; Akemi Muraoka, Kure, all of Japan

[73] Assignee: Mazda Motor Corporation, Hiroshima-ken, Japan

[21] Appl. No.: 362,270

[22] Filed: Dec. 22, 1994

[30] Foreign Application Priority Data

Dec. 27, 1993 [JP] Japan .................. 5-332948
Feb. 17, 1994 [JP] Japan .................. 6-020520

[51] Int. Cl.$^6$ .............. C01B 7/07; C07D 307/89
[52] U.S. Cl. .................. 423/488; 549/250
[58] Field of Search ............. 423/488; 549/250; 588/213, 216, 226, 228, 241

[56] References Cited

U.S. PATENT DOCUMENTS

| | | | |
|---|---|---|---|
| 3,829,558 | 8/1974 | Banks et al. | 588/213 |
| 4,119,645 | 10/1978 | Auroy et al. | 549/250 |
| 4,328,152 | 5/1982 | Tsigdinos et al. | 524/406 |
| 4,458,095 | 7/1984 | Wingfield, Jr. et al. | 588/216 |
| 4,485,244 | 11/1984 | Fox et al. | 549/250 |
| 5,464,602 | 11/1995 | Evans et al. | 423/488 |
| 5,608,136 | 3/1997 | Maezawa et al. | 588/228 |

FOREIGN PATENT DOCUMENTS

| | | | |
|---|---|---|---|
| 619268 | 10/1994 | European Pat. Off. | 423/488 |
| 659868 | 6/1995 | European Pat. Off. | |
| 47-32509 | 8/1972 | Japan | 423/488 |
| 48-55492 | 1/1975 | Japan | 423/488 |
| 53-60974 | 5/1978 | Japan | |
| 1350727 | 4/1974 | United Kingdom | 423/488 |

OTHER PUBLICATIONS

Bond, G. C. et al, "Catalysed Destruction of Chlorinated Hydrocarbons", J. Appl. Chem. Biotech., 25, 1975, no month, pp. 241–248.

*Primary Examiner*—Steven Bos
*Attorney, Agent, or Firm*—Morrison & Foerster LLP

[57] ABSTRACT

There is provided a process to recover phthalic anhydride from a plastic material which contains a phthalate ester as a plasticizer comprising the steps of:

(a) heating the plastic material so that the plastic material is gasified to produce a first product, (b) contacting the first product with alumina catalyst so that the product is catalytically cracked to produce a first catalytically cracked product comprising phthalic anhydride; and (c) recovering phthalic anhydride from the first catalytically cracked product.

9 Claims, 13 Drawing Sheets

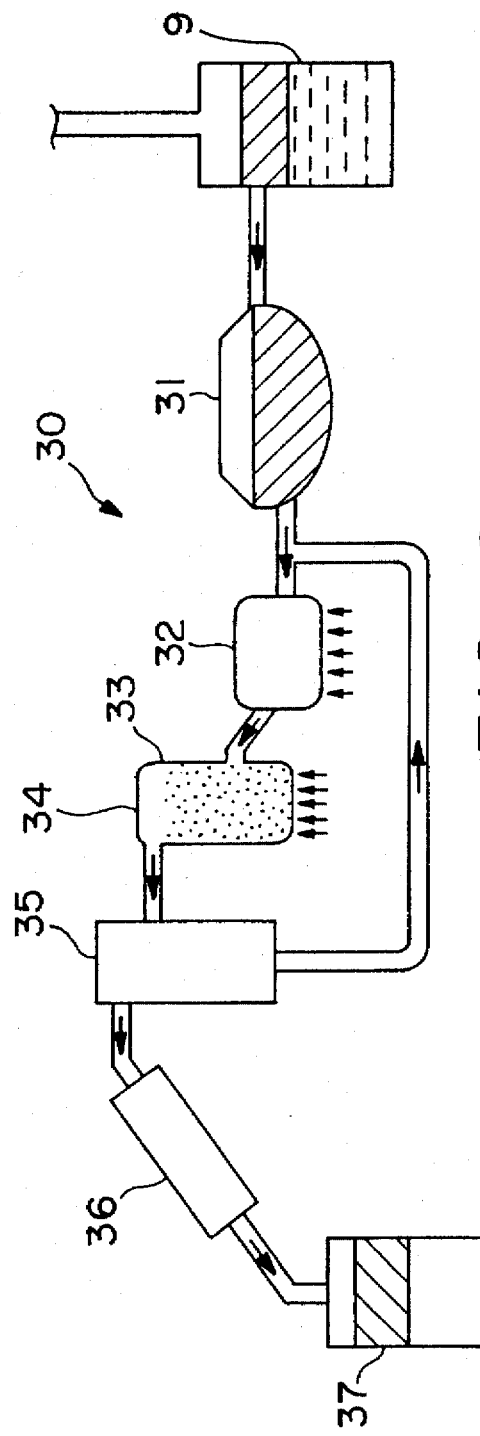
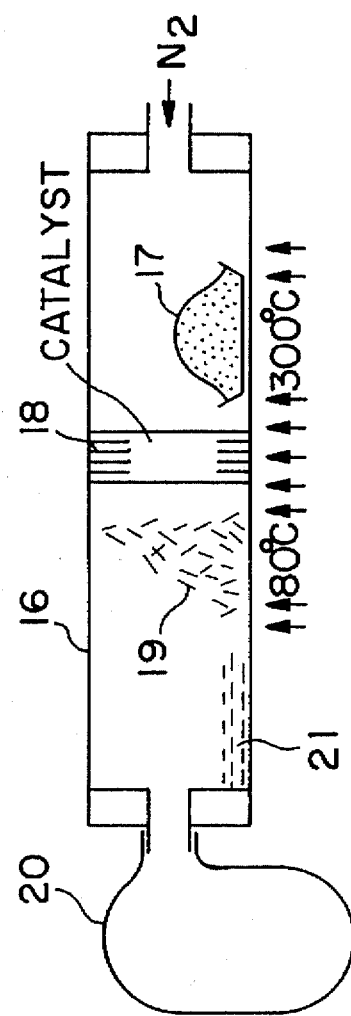

γ-ALUMINA CATALYST CASE   NEEDLE-LIKE CRYSTAL

| RESIDUE AFTER CRACKING 4.3g | GAS COMPONENT 4.8g | 0.9g |

FIG. 4A

ZEOLITE CATALYST CASE   NEEDLE-LIKE CRYSTAL

| RESIDUE AFTER CRACKING 4.1g | GAS COMPONENT 4.9g | 1.0g |

FIG. 4B

NO CATALYST CASE   NEEDLE-CRYSTAL 0.3g

| RESIDUE AFTER CRACKING 4.2g | GAS COMPONENT 3.5g | | |

LIQUID COMPONENT 2.0g

FIG. 4C

AGED γ-ALUMINA CATALYST CASE   NEEDLE-LIKE CRYSTAL 0.7g

| RESIDUE AFTER CRACKING 4.1g | GAS COMPONENT 3.8g | 1.4g | |

LIQUID COMPONENT

FIG. 4D

AGED ZEOLITE CATALYST CASE   NEEDLE-LIKE CRYSTAL 0.4g

| RESIDUE AFTER CRACKING 4.3g | GAS COMPONENT 3.3g | | |

LIQUID COMPONENT 2.0g

PROCESS FOR RECOVERING PHTHALIC ANHYDRIDE AND HYDROGEN CHLORIDE FROM PLASTIC MATERIALS

BACKGROUND OF THE INVENTION

1. Field of the Invention

The present invention relates to a process of cracking a plastic material into useful components and recovering them. In addition, the present invention also relates to an apparatus of carrying out the process according to the present invention. The term "plastic material" is intended to mean, in addition to, a plastic material such as a general-purpose plastic material and an engineering plastic material, a rubber material. Such a plastic material may be of any type for example, a waste material.

2. Description of the Related Art

Japanese Patent Kokai Publication No. 53-60974 describes a process in which a waste plastic material such as a polyvinyl chloride plastic material is supplied into a retort, which is heated to a temperature of not higher than 350° C. so as to thermally decompose the material; a distilled organic material comprising a plasticizer and its cracked materials are burnt off while produced chlorine gas is recovered; and activated carbon is recovered from a residue comprising carbonaceous material after cracking.

When a chlorine containing plastic material such as a polyvinyl chloride is thermally decomposed and formed chlorine gas is recovered as described above, effective source utilization is achieved by reusing the recovered chlorine gas. However, since a plasticizer mainly comprising a phthalate ester contained in the plastic material cannot be effectively cracked, it is burnt off, for example, in a low temperature gasification combustion process.

Thus, there is a problem that an industrial useful material such as phthalic anhydride which constitutes the phthalic ester plasticizer cannot be utilized by the process as described above, so that not, only sources are wasted but also such an effective material is degraded due to contamination by the plasticizer and its cracked components. In addition, an aliphatic hydrocarbon produced with cracking of the plasticizer such as octanol is reacted with a chlorine compound such as hydrogen chloride from the plastic material, whereby a chlorinated hydrocarbon such as octyl chloride is produced of which disposal causes a problem.

SUMMARY OF THE INVENTION

It is, therefore, an object of the present invention to overcome the above problems and provide a process of effectively cracking an plastic material which contains a phthalate ester as a plasticizer (such as a waste plastic material and/or a waste rubber material) and recovering phthalic anhydride (and optionally other compound such as hydrogen chloride, hydrocarbons and so on) from a cracked product, so that the recovered anhydride (and optionally other compound such as hydrogen chloride, hydrocarbons and so on) can be reused.

It is another object of the present invention to provide an apparatus which performs the process of the present invention described just above.

According to the first aspect of the present invention, there is provided a process to recover phthalic anhydride from a plastic material which contains a phthalate ester as a plasticizer comprising the steps of:

(a) heating the plastic material so that the plastic material is gasified to produce a first product, (b) contacting the first product with alumina catalyst so that the product is catalytically cracked to produce a first catalytically cracked product comprising phthalic anhydride; and (c) recovering phthalic anhydride from the first catalytically cracked product.

In one embodiment of the process of the first aspect according to the present invention, the plastic material consists essentially of or comprises a chlorine containing plastic material and the process further comprises step (d) of recovering hydrogen chloride after step (c) which is produced by the gasification in step (a).

In another embodiment of the process of the first aspect according to the present invention; the plastic material consists essentially of or comprises a chlorine-containing material and the process comprises, in addition to step (d), the steps of (e) gasifying hydrocarbon chlorides produced in steps (a) and (b) due to the presence of hydrogen chloride;

(f) converting the gasified chlorides to hydrogen chloride and hydrocarbons by catalytically cracking the chlorides through solid acid catalyst so that a catalytically cracked product is produced; and (g) recovering the hydrocarbons from the catalytically cracked product.

In a further embodiment of the first aspect according to the present invention, the process further comprises steps of (h) heating a residue from the plastic material which is left after step (a) so that the residue is gasified to have a second product, (i) contacting the second product with solid acid catalyst so that the second product is catalytically cracked to produce a second catalytically cracked product comprising lower boiling point hydrocarbons; and (j) recovering the lower boiling point hydrocarbons from the second catalytically cracked product.

In the above embodiment, step (i) is preferably carried out using alumina catalyst.

In the second aspect, the present invention provides an apparatus for the above process of the first aspect which recovers useful materials from the plastic material.

There is thus provided an apparatus for recover phthalic anhydride by cracking a plastic material which contains a phthalate ester as a plasticizer, which apparatus comprises a first heating chamber which heats to gasify the plastic material to produce a first product;

a first catalyst vessel which contains alumina catalyst so as to catalytically crack the first product from the heating chamber to produce a first cracked product; and a first recovery zone which recovers phthalic anhydride from the first cracked product.

In one embodiment of the second aspect of the present invention, the plastic material consists essentially of or comprises a chlorine containing plastic material and the apparatus further comprises a second recovery zone which recovers hydrogen chloride present in the first cracked product of which phthalic anhydride has been recovered in the first recovery zone.

In a preferred embodiment of the apparatus just described above, the apparatus further comprises a conversion heating chamber which heats and gasifies a hydrocarbon stream containing hydrocarbon chlorides obtained from the second recovery zone to produce a gasified product;

a conversion catalyst vessel containing solid acid catalyst which catalytically cracks the chlorides to produce a cracked product comprising lower boiling point hydrocarbons; and a conversion recovery zone which recovers the lower boiling point hydrocarbons from the cracked product.

In another embodiment of the second aspect of the present invention, the apparatus further comprises a second heating chamber in which a residue left after cracking in the first heating chamber is heated to gasify to produce a second product;

a second catalyst vessel which contains solid acid catalyst so as to catalytically crack the second product from the second heating chamber to produce a second cracked product; and a third recovery zone which recovers lower boiling point hydrocarbons from the second cracked product.

BRIEF DESCRIPTION OF THE DRAWINGS

FIG. 2 schematically shows an apparatus (or a process flow sheet of the process) for the conversion system according to the present invention;

FIG. 3 schematically shows an apparatus which was used for carrying out Examples which will be explained later;

FIG. 4A is a graph which shows amounts of products produced in Example 1 in which γ-alumina catalyst was used;

FIG. 4B is a graph which shows amounts of products produced in Example 2 in which zeolite catalyst was used;

FIG. 4C is a graph which shows amounts of products produced in Example 3 in which no catalyst was used;

FIG. 4D is a graph which shows amounts of products produced in Example 4 in which hydrogen chloride aged γ-alumina catalyst was used;

FIG. 4E is a graph which shows amounts of products produced in Example 5 in which hydrogen chloride aged zeolite catalyst was used;

DETAILED DESCRIPTION OF THE INVENTION

Figure 1:
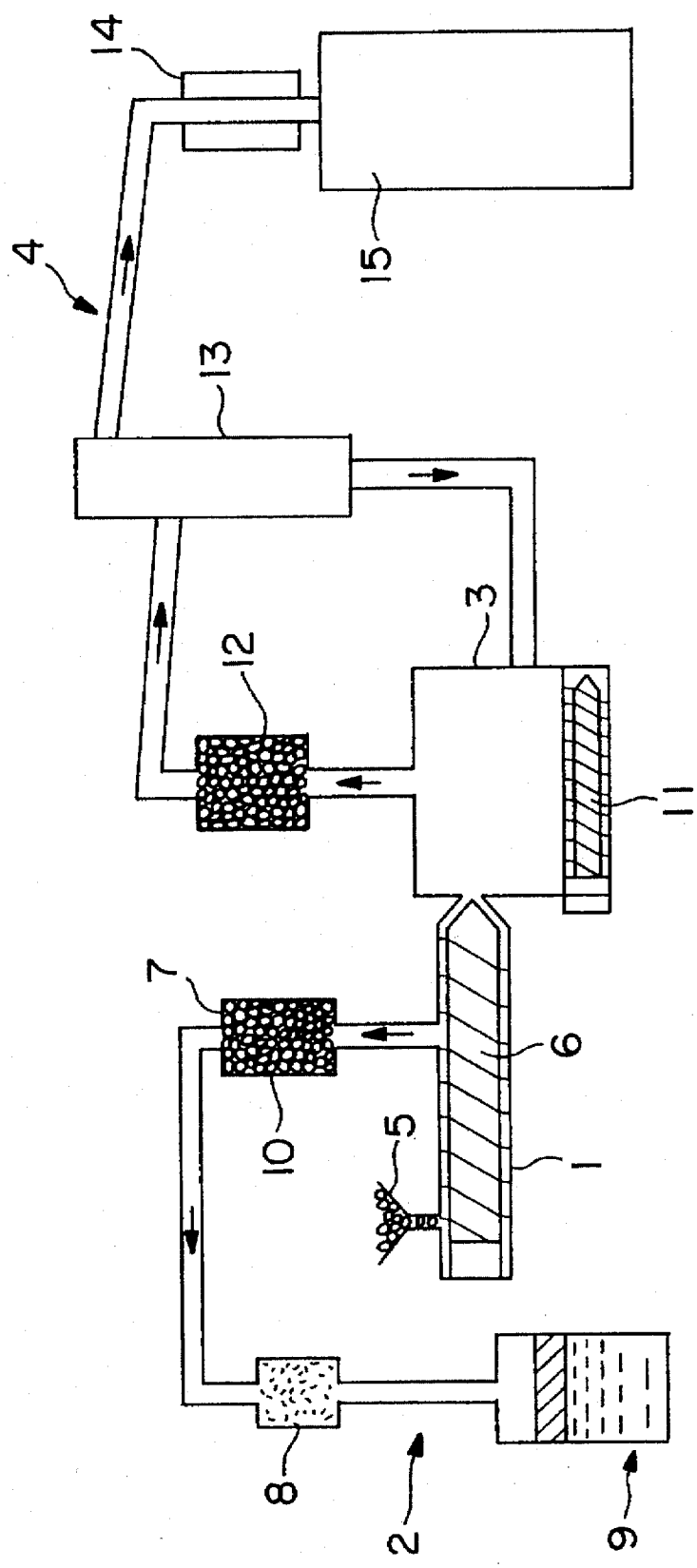
FIG. 1 schematically shows an apparatus (or a process flow sheet of the process) according to the present invention.

In the present invention, "gasify" in step (a) means that the plastic material containing the phthalate ester is so heated that the plasticizer contained therein is vaporized and at least partially thermally cracked and the plastic material itself is partially thermally cracked.

A temperature to which the plastic material is to be heated in step (a) depends on a type of the plastic material. However, the temperature is typically in the range of 220° to 350° C. and preferably 250° to 300° C.

According to the first aspect, when the phthalate ester is heated, usually not only the ester is vaporized but also the ester is at least partially cracked into phthalic acid and an alcohol component corresponding to an alkyl group of the ester, and also other hydrocarbons such as a dehydrated compound from the alcohol, cracked hydrocarbon from the alcohol and so on are formed. For example, when dioctyl phthalate is heated, octanol and octene may be formed in addition to phthalic acid. Usually, the formed phthalic acids is immediately dehydrated so that phthalic anhydride is produced.

According to the first aspect, when the plastic material is heated, various kinds of hydrocarbons are produced due to thermal cracking depending on the temperature to be heated while a residue of the plastic material (referred to as "residue after cracking") is left. In addition, in the case where the plastic material is of a type of a chlorine-containing material or a chlorinated material (namely, chlorine atoms are chemically bonded therein) such as a polyvinyl chloride, hydrogen chloride and/or a chlorinated hydrocarbon are additionally produced due to the thermal cracking. The produced hydrogen chloride may react with the hydrocarbons present in a system (for example, octanol), whereby other chlorinated hydrocarbons (octyl chloride) may be formed.

Therefore, "first product" in step (a) comprises the vaporized plasticizer (phthalate ester) itself, phthalic anhydride formed from thermally cracked phthalate ester and various kinds of hydrocarbons optionally including their chlorides.

When such a product is contacted with the alumina catalyst in step (b), the phthalate ester is catalytically cracked into phthalic acid and hydrocarbons such as an alcohol component from the ester and dehydrated compound of the alcohol and so on (as in the thermal cracking in step (a)). Similarly, phthalic anhydride is produced from the produced phthalic acid. In addition to the formation of phthalic anhydride and the hydrocarbons, lower molecular weight hydrocarbons are formed in step (b) from the hydrocarbons from step (a) and the hydrocarbons formed by the catalytically cracking of the phthalate ester. These procedures in step (b) are, in principle, the same as those during the thermal cracking of step (a). Only the difference between steps (a) and (b) is whether "thermally cracking" or "catalytically cracking". Thus, in step (b), almost all of the phthalic ester present therein is cracked into phthalic anhydride. Thus, the catalytically cracked product comprises phthalic anhydride and the various hydrocarbons.

Step (a) is usually carried out under an atmosphere without oxygen so as to avoid formation of undesired oxides. Thus, for example, step (a) may be carried out under an inert atmosphere comprising an inert gas such as nitrogen. Alternatively, step (a) may be carried out in a condition of a vacuum pressure. An operating pressure is not specifically limited and any pressure may, in principle, be used for step (a). Usually, step (a) is operated under around an atmospheric pressure.

In the present invention, the plastic material containing the phthalate ester includes a general-purpose plastic material, an engineering plastic material and a rubber material and any other so-called plastic material which contains a phthalate ester as the plasticizer. It is, of course, possible to combine any two or more plastic materials in the present invention.

The general-purpose plastic material includes, for example, a polyethylene, a polypropylene, a polystyrene, a poly(acrylonitrile-butadiene-styrene), a polymethyl methacrylate, polyvinyl alcohol, a polyvinyl chloride and so on.

The engineering plastic material includes, for example, a polyamide, a polyacetal, a polycarbonate, a polyphenylene ether, a polybutylene terephtalate, a polysulfone, a polyether sulfone, a polyphenylene sulfide, a polyarylate, a polyimide, a polyamide imide, a polyether ether ketone and so on.

The rubber material includes a synthesized rubber such as a styrene-butadiene rubber, a high styrene rubber, a butadiene rubber, an isoprene rubber, an ethylene-propylene rubber, an ethylene-propylene-diene rubber, an acrylonitrile-butadiene rubber, a chloroprene rubber, a butyl rubber, an urethane rubber and so on and a natural rubber.

In the present invention, the plastic material contains the phthalate (ester) as a plasticizer, and such a phthalate which is conventionally used for various kinds of the plastic materials as described above includes a di-normal alkyl phthalate, a di-isoalkyl phthalate and a mixed alkyl phthalate. Thus, two alkyl groups of the phthalate may be the same or different from each other.

In the present invention, the plastic material may contain any one or more conventional phthalate esters. Thus, there is no specific limitation of the phthalate, and the alkyl group of the phthalate contains preferably 1 to 12 carbon atoms, more preferably 4 to 9 carbon atoms. For example, the phthalate may be dinonyl phthalate, dioctyl phthalate, dibutyl phthalate, di-2-ethyl hexyl phthalate or a mixture thereof.

In the first aspect of the present invention, step (b) may be carried out under operation conditions which are substantially the same as those in step (a). Namely, the catalytic cracking may be carried out at a temperature in the range of 220° to 350° C., preferably in the range of 250° to 350° C. under around a normal pressure in an atmosphere without oxygen.

In the first aspect of the present invention, the catalyst in step (b) may be any type of alumina catalyst such as γ-alumina, which mainly cracks the phthalate into phthalic acid and a corresponding alcohol. The produced phthalic acid is immediately converted to phthalic anhydride under the conditions of step (b). Some of the produced alcohol is further cracked to a corresponding alkene, further lower hydrocarbons such as an aliphatic hydrocarbon and an aromatic hydrocarbon. It is, of course, possible that some of the product from step (a) is also cracked into further lower hydrocarbons. Thus, a effluent from step (b) (i.e. the first catalytically cracked product) comprises phthalic anhydride and the hydrocarbons such as the corresponding alcohol, alkene and any other lower hydrocarbons and optionally hydrogen chloride and chlorides.

In order to carry out step (c), the effluent from step (b) is cooled to a temperature in the range of 80° to 200° C., preferably gradually cooled from its inherent temperature when it leaves step (b) toward about 80°–200° C., more preferably toward 80° C., so that a needle-like crystal of phthalic anhydride is precipitated on, for example, a cooler surface, and then the crystal is recovered.

Any proper cooling means may be used in step (c). For example, the effluent may by passed through a cooling fin equipped cooler. The deposited crystal may be wash recovered as an alkaline salt using an alkaline solution such as a sodium hydroxide solution. The recovered phthalic anhydride or its salt can be used in any possible application optionally after additional treatment.

In one embodiment of the first aspect of the present invention, the plastic material may further comprise or consist essentially of a polyvinyl chloride plastic. In this embodiment, when the plastic material is heated to gasify, chlorine which has been chemically bonded to the plastic material is liberated and formed into hydrogen chloride. Some of the produced hydrogen chloride reacts with the hydrocarbons from the thermal cracking of the plasticizer and the plastic material such as an alcohol and an alkene and other hydrocarbons to produce chloride compounds such as an alkyl chloride and an alkene chloride.

Therefore, in this embodiment, the product in step (a) further comprises hydrogen chloride and the chloride compounds in addition to the other components as described above. These chloride compounds substantially have no adverse effect on the catalytically cracking in step (b). It is, of course, possible that some of hydrogen chloride reacts with compounds produced in step (b) to further produce chlorides.

In step (c), the effluent (i.e. the first cracked product from step (b)) is cooled as described above. Then, the deposited phthalic anhydride is recovered and the rest of the effluent mainly comprising the lower cracked hydrocarbons and optionally hydrogen chloride and the chlorides is supplied into an aqueous phase so that soluble hydrocarbon and optional hydrogen chloride is recovered in a hydrochloric acid solution (this step is referred to as step (d)). Non-dissolved lower hydrocarbons and chlorides are separated into an upper organic phase which is positioned on the aqueous phase. The aqueous phase containing hydrogen chloride can be treated in any conventional manner so as to reuse or dispose. As to the organic phase, it may be also treated in any conventional manner so as to reuse or dispose the chloride and the lower hydrocarbon. Alternatively, the rest of the effluent may be supplied into any suitable absorber means using an aqueous phase.

The upper organic phase may be recovered and reused, for example, as a fuel oil or any other feed material especially when the organic phase does not contain the chlorides.

However, when the organic phase contains the chlorides, the organic phase is preferably heated to gasify so that a gasified product is obtained which comprises vaporized hydrocarbons and vaporized chlorides as well as optionally, depending on the heating temperature, thermally cracked hydrocarbons and thermally cracked chlorides are produced. This gasification is referred to as step (e). In step (e), the organic phase is heated to any temperature so as to make following step (f) proceed conveniently. For example, the temperature may be above 300° C. Preferably, it is in the range of 350° to 400° C. However, the organic phase is not necessarily vaporized, and step (e) may be eliminated provided that step (f) also has a function of step (e) (i.e. vaporization function).

The gasified product is then supplied to step (f) in which catalyst comprising solid acid catalyst such as alumina catalyst thermally cracks the hydrocarbons and the chlorides into a converted product comprising lower boiling point hydrocarbons and hydrogen chloride. It should be noted that an amount of the chloride in the converted product is usually small. The converted product from step (f) may be treated with an aqueous phase in step (g) as in the case of the treatment of the effluent from step (d), whereby hydrogen chloride is recovered as hydrochloric acid and also the lower boiling point hydrocarbons which are not dissolved in the aqueous phase is recovered as a lower hydrocarbon oil (low boiling point hydrocarbon oil). Conditions of steps (e) and (f) may be substantially similar each other. For example, in step (f), the temperature may be 300° C. or higher and the pressure may be an atmospheric pressure without oxygen.

The recovered aqueous hydrochloric acid solution may be treated in a conventional manner separately as in the case of the aqueous solution from step (d). Alternatively, the aqueous hydrochloric acid solution may be added to the aqueous hydrochloric acid solution of step (d) and both solutions may be treated together. The recovered hydrocarbons which does not contain a substantive amount of the chlorides may be used in any application such as a fuel.

Not bound by any theory, it is contemplated that since there is little hydrogen chloride in the organic phase which enters step (e) due to the removal thereof by the previous step (d), chloride is hardly formed in step (f) when the chemical equilibrium is considered. When an amount of the chlorides contained in the effluent from step (f), the effluent may be fractionated so that the chlorides are separated, which may be returned to step (e) or (f).

In another embodiment of the first aspect of the present invention, a residual plastic material (i.e. residue after cracking), which is left in step (a) after the thermal cracking and the vaporization of the phthalic ester and the thermal cracking of the plastic material, is further subjected to a second thermal cracking in step (h) which is operated at a higher temperature than that of step (a), whereby the residue is additionally thermally cracked to produce a second product comprising any possible hydrocarbon from the plastic material residue due to the thermal cracking.

The temperature at which step (h) is carried out is higher than that of step (a), and usually a temperature is higher than 350° C., preferably in the range of 350° to 550° C. and more preferably around 500° C. The other conditions such as an operation pressure and an atmosphere may be substantially the same as those in step (a).

The second product produced in step (h) is subjected to step (i) in which catalytically cracking of the second product is carried out in the presence of a solid acid catalyst to produce a second cracked product. The catalyst may comprise at least one of alumina catalyst and zeolite catalyst. Operation conditions of step (i) such as an operation pressure and an operation temperature may be substantially the same as those in step (h). Preferably, the temperature is in the range of 500° to 550° C. The second cracked product from step (i) comprises various kinds of further cracked hydrocarbons, for example, those having carbon atoms in the range of 2 to 34.

The effluent of step (i) is then subjected to step (j) in which the effluent (i.e. the second cracked product) is fractionated into a lower hydrocarbon stream and a higher hydrocarbon stream by, for example, a distillation column or any other means having a fractionation function. For this fractionation, any conventional means such as a tray or packed distillation column may be used as in other fractionation purposes There is no specific cut point in step (j). For example, the lower hydrocarbon stream comprising hydrocarbons which have carbon atoms up to 19 may be separated from the higher hydrocarbon stream comprising hydrocarbons which have carbon atoms of 20 or more. The lower hydrocarbon stream may be recovered as a hydrocarbon oil, which can be used for various purposes such as a fuel. The higher hydrocarbon stream may be recycled to step (h) to thermally and catalytically crack again through steps (h) and (i).

The catalyst in step (i) may be any solid acid catalyst. For example, alumina catalyst and zeolite catalyst may be used. In one embodiment, the zeolite catalyst is preferred since its cracking activity is usually larger than that of the alumina catalyst. Though the zeolite catalyst is less resistant to hydrogen chloride, there is produced substantially no hydrogen chloride in step (h) since almost all of hydrogen chloride has been produced in step (a) even in the case in which a choline containing plastic material is used in step (a). Therefore, the catalyst in step (i) is not subjected to an atmosphere comprising hydrogen chloride, so that the zeolite catalyst can be effectively used in step (i).

However, in another embodiment, the alumina catalyst may be also advantageously used in which not so low molecular weight hydrocarbons are to be obtained by the catalytically cracking.

The lower hydrocarbon stream from step (j) is cooled in step (k) in which a portion of the stream is liquified, which is recovered in step (l) in which the liquified steam is supplied to an aqueous phase to dissolve the soluble components into such a phase and obtain a lower boiling point hydrocarbon phase on the aqueous phase. The hydrocarbon phase may be recovered from step (k) and used in various applications.

DESCRIPTION OF THE PREFERRED EMBODIMENTS

The present invention will be, hereinafter, further described by way of one preferred embodiment with reference to accompanying drawings.

Referring to FIG. 1, there is shown an apparatus which carries out the process according to the present invention in which the plastic material is heated and cracked so as to recover useful materials. The apparatus comprises a first cracking system 2 which comprises a first heating chamber 1 for carrying out step (a) and a second cracking system 4 which comprises a second heating chamber 3 for carrying out step (h).

The first heating chamber 3 comprises a hopper 5 to which a waste plastic material is supplied after grinding if necessary, a heating means (not shown) which heats the plastic material containing a plasticizer so as to gasify the same, a transfer means 6 such as conveyer belt which transfers a plastic material residue, which is left after the gasification in the chamber 1, to the second heating chamber 3.

The heating means heats the plastic material such as polyvinyl chloride material and/or a chlorinated rubber material to a temperature at which the phthalate plasticizer comprising, for example, dioctyl phthalate (DOP), dibutyl phthalate (DBP), dimethyl phthalate (DMP) and diethyl phthalate (DEP) and the plastic material containing the plasticizer are gasified. Preferably, the heating means so heats the plastic material that most of, preferably all of the plasticizer is vaporized and/or thermally cracked and at least a portion of the plastic material is thermally cracked. Particularly, in the case of the chlorine-containing plastic material, heating liberates most of, preferably substantially all of chlorine atoms from the plastic material to form hydrogen chloride in step (a). Generally, the heating means heats the plastic material to a temperature at which the plasticizer is gasified and chlorine is liberated but the rest is not cracked as much as possible. For example, the temperature is not higher than 350° C., preferably not higher than 300° C. in step (a).

The first cracking system 2 comprises also a first catalyst vessel 7 in which step (b) is carried out; a first recovery zone 8 in which step (c) is carried out by cooling a gaseous effluent from the vessel 7 to a temperature in the range of 80° to 200° C. so as to precipitate a needle-like crystal of phthalic anhydride from the gaseous effluent from step (b) and recover the crystal; and a second recovery zone 9 in which step (d) is carried out by supplying a residual gas thereto from step (c) so that hydrogen chloride, in the case of the chlorine-containing plastic material such as a polyvinyl chloride, in an aqueous phase and a lower boiling point hydrocarbon phase (mainly aliphatic hydrocarbons) are recovered from the residual gas, respectively.

The vessel 7 contains solid acid catalyst comprising alumina catalyst 10, preferably chlorinated alumina catalyst which is preferably maintained at a temperature of 300° to 350° C. so as to catalytically crack mainly the plasticizer contained in the gaseous product from step (a) into phthalic anhydride and lower hydrocarbon components such as octene and butene.

The first recovery zone 8 is kept at a temperature in the range of 80° to 200° C. so as to cool the gaseous effluent from step (b) and precipitates phthalic anhydride as the needle-like crystal which is collected in a relevant manner while the rest of the gaseous effluent is discharged into the second recovery zone 9.

The second recovery zone 9 recovers, as hydrochloric acid, hydrogen chloride in the discharged gaseous effluent by introducing it into an aqueous phase so as to dissolve hydrogen chloride therein. In addition, a hydrocarbon phase comprising the lower hydrocarbons is formed on the aqueous phase by liquefying the gaseous effluent in the zone 9. The hydrocarbon phase may be taken out of zone 9 and used as a fuel oil or a naphtha feed.

The second heating chamber 3 is used for carrying out step (h) and it comprises a heating means (not shown) which heats the residue transferred from the chamber 1 to a temperature of, for example, around 500° C. so as to further gasify the residue; and a discharging means 11 which discharges the residue left without being gasified in step (h).

The second cracking system 4 further comprises a second catalyst vessel 12 in which step (i) is carried out; a fractionation means 13 (such as a conventional distillation column) in which step (j) is carried out so as to fractionate a gaseous effluent from step (i); a cooler 14 which cools a gaseous effluent from the fractionation means 13 to liquefy at least a portion of the effluent to produce a lower hydrocarbon oil; and a third recovery zone 15 which recovers the oil.

The catalyst vessel 12 contains therein a solid acid catalyst such as at least one of alumina catalyst and zeolite catalyst. The fractionation means 13 divides the effluent comprising various hydrocarbons from step (i) into a higher hydrocarbon stream (which comprises higher boiling point hydrocarbons) and a lower hydrocarbon stream (which comprises lower boiling point hydrocarbons) and leads the lower hydrocarbon stream in the gaseous phase to the cooler 14. At the same time, the means 13 returns the higher hydrocarbon stream comprising a tar-like material and/or a wax-like material to the second heating chamber 3 so as to treat in step (h) again.

The cooler 14 cools the gaseous effluent from the fractionation means 13 to form a vapor-liquid mixture, which is introduced to the third recovery zone 15. The recovery zone 15 collects the liquified hydrocarbon as a hydrocarbon oil on an aqueous phase while leads non-liquified hydrocarbon to a gas holder (not shown).

The plastic material supplied to the hopper 5 has been finely divided into a predetermined size for the purpose of effective gasification in steps (a) and (h).

One embodiment of the present process will be explained in detail in which an organic material is thermally cracked and useful components are recovered with using the apparatus as described above.

The organic material comprising a waste plastic material ground into a predetermined size is supplied into the hopper 5 and the material is heated to a predetermined temperature while it is transferred with the transfer means 6, so that the material containing the plasticizer is gasified to produce a gaseous first product (step (a)). The gaseous first product produced in the first heating chamber 1 becomes an upward stream comprising some mist and enters the first catalyst vessel 7.

The stream is contacted with the alumina catalyst 10 contained in the vessel 7 so that the phthalate ester contained in the stream is catalytically cracked to produce the following components (step (b)).

For example, when the plasticizer is DOP, it is cracked into phthalic anhydride and aliphatic hydrocarbons such as octanol and octene while a portion of the aliphatic hydrocarbons is reacted with hydrogen chloride if any to produce chlorinated aliphatic hydrocarbons such as octyl chloride. When the plasticizer is, for example, DBP, it is cracked into phthalic anhydride and aliphatic hydrocarbons such as butanol and butene while a portion of the aliphatic hydrocarbons is reacted with hydrogen chloride if any to produce chlorinated aliphatic hydrocarbons such as butyl chloride.

By supplying to and cooling in the first recovery zone 8 a gaseous stream discharged from the vessel 7 (i.e. a first cracked product comprising phthalic anhydride, hydrogen chloride, hydrocarbons and hydrocarbon chlorides), phthalic anhydride in the stream is precipitated and recovered while the rest of the stream is supplied to the second recovery zone 9. In this second recovery zone 9, hydrogen chloride contained in the rest is separated from the lower hydrocarbons and their chlorides. For example, hydrogen chloride is recovered as hydrochloric acid solution and the lower hydrocarbons and the chlorides are recovered as an organic phase on the aqueous solution.

On the other hand, the residue of the plastic material which has not completely thermally cracked in step (a) is supplied to the second heating chamber 3 by the transfer means 6 and the residue is gasified at a temperature which is higher than that of the first heating chamber 1 to produce a second product in a gaseous stream. The second product gaseous stream is discharged to a second catalyst vessel 12 containing a solid acid catalyst so that the product is catalytically cracked into a second cracked product comprising lower molecular weight hydrocarbons. The vessel 12 contains at least one of alumina catalyst and zeolite catalyst as the solid acid catalyst. The second cracked product from the vessel 12 is supplied to a fractionation means 13 to separate the lower hydrocarbon stream comprising the lower molecular weight hydrocarbons from the rest thereof, which is then passed through a cooler 14 and a third recovery zone 15.

In the cooler 14, some of the low boiling point hydrocarbons are liquified as a lower boiling point hydrocarbon oil which may be recovered in the third recovery zone 15. The higher boiling point hydrocarbons separated in the fractionation means 13 (i.e. the rest) is recycled to the second heating chamber 3, which is again heated and catalytically cracked into low molecular weight hydrocarbons to be recovered.

As described above, since phthalic anhydride and the low boiling point hydrocarbons are recovered from the plastic material by thermally cracking and catalytically cracking, respectively, the recovered phthalic anhydride and the lower hydrocarbons are effectively used. It should be noted that the recovered phthalic anhydride is not contaminated with the lower boiling point hydrocarbons and vice versa, which is advantageous for the next applications.

In addition, hydrogen chloride produced from the thermal cracking of the plastic material, the hydrocarbons which is originated from the plastic material and the plasticizer and the chlorides produced by a reaction of hydrogen chloride with the hydrocarbons are recovered in the second recovery zone 9, so that they are effectively used in a predetermined application. Since the produced phthalic anhydride is recovered in the first recovery zone 8, the lower boiling point hydrocarbon oil does not contain an amount of phthalic anhydride, which improves a quality of the lower boiling point hydrocarbon.

When the second cracking system 4 comprising the second heating chamber 3 and the second catalyst vessel 12 is employed, the plastic material is effectively cracked while each equipment of the second cracking system 4 is protected from corrosion due to hydrogen chloride in the case in which the plastic material comprises the chlorine-containing plastic material.

Namely, since the first heating chamber 1 is controlled at a temperature not higher than 350° C. at which bonded chlorine can be sufficiently liberated as hydrogen chloride in order to prevent hydrogen chloride from being liberated at a higher temperature, the plastic material cannot be completely cracked, so that a fairly large amount of the plastic material may be left without being cracked after the thermal cracking in step (a) (the residue after cracking). However, such a residue may be cracked at a higher temperature such as 500° C. in the second heating chamber 3 so as to gasify and convert the residue to lower molecular weight hydrocarbons, which can be recovered thereafter.

Since the chlorine component contained in the plastic material is liberated in the first heating chamber 1 as hydrogen chloride which is recovered thereafter, such a chlorine component does not supplied to the second heating chamber 2. Therefore, even when the second heating chamber is set to heat the plastic material to a higher temperature, the equipments constituting the second cracking system 4 are not subjected to the corrosion problem due to hydrogen chloride.

In addition, the second catalyst vessel 12 may contain the solid acid catalyst 10 comprising alumina which is resistant to hydrogen chloride, and in such a case, the catalyst is thus hardly degraded, so that its activity can be kept over an extended period. Further, the alumina catalyst has a less hydrocarbon cracking activity than that of zeolite catalyst. Therefore, since the hydrocarbons which has been produced in the second heating chamber 3 and which enters the vessel 12 are not cracked to excessively lower molecular weight hydrocarbons (such as propane and propene) and/or not converted to aromatic hydrocarbons other than required, hydrocarbons having a not so lower molecular weight are recovered as an aliphatic hydrocarbon oil which can be used in various applications.

To the contrary, since the catalyst contained in the second catalyst vessel is not adversely affected by hydrogen chloride due to its absence, the zeolite catalyst may be used in the vessel 12 in another embodiment. Therefore, the zeolite catalyst which is less resistant to hydrogen chloride than alumina catalyst and which is higher cracking activity than alumina catalyst can be used when the hydrocarbons are to be cracked into a further lower molecular weight hydrocarbons.

As described above, even when the plastic material contains the chlorine component, the present invention can effectively treat the material and recover phthalic anhydride, hydrogen chloride and the lower boiling point hydrocarbon oil. When the plastic material does not comprise the chlorine containing material, there is, of course, no need for the recovery of hydrogen chloride in the second recovery zone 9.

Alternatively, by eliminating the second cracking system 4, only phthalic anhydride may be recovered in the first cracking system 2. Further, it is also possible to recover phthalic anhydride, hydrogen chloride produced by thermally cracking the chlorides and the lower boiling point hydrocarbon oil, respectively.

In another embodiment as shown in FIG. 2 which shows a conversion system 30, the chlorides of the lower boiling point aliphatic hydrocarbons are converted to the lower boiling point aliphatic hydrocarbons, which is to be recovered. The system 30 comprises a vessel 31 which stores the upper organic phase from the second recovery zone 9 mainly comprising the aliphatic hydrocarbons and the hydrocarbon chlorides; heating chamber 32 in which the organic phase is gasified to produce a gasified product (i.e., vaporized and partially thermally cracked) (step (e)); a conversion catalyst vessel 34 containing solid acid catalyst 33 such as alumina in which the gasified product from the chamber 32 is catalytically cracked (step (f)); a fractionation means 35 which fractionates a cracked stream discharged from the vessel 34 into a gaseous lower boiling point hydrocarbon stream and a higher boiling point hydrocarbon stream comprising remaining chlorides if any; a cooler 36 which cools the lower gaseous stream; and a fourth recovery zone 37 which recovers liquid components liquified in the cooler 36 (step (g)).

The organic phase is heated so as to be vaporized in the vessel 32 by a heating means (not shown), whereby a gaseous product is produced comprises the hydrocarbons such as octene and the chlorides. The temperature to which the organic phase is heated is not specifically limited provided that the organic phase is vaporized. For example the temperature may be around 300° C. or higher. Then the produced gaseous product is passed through the vessel 34 containing alumina catalyst 33 with keeping its temperature so that the chlorides in the gaseous product is catalytically cracked into aliphatic hydrocarbons and hydrogen chloride.

Then, the cracked aliphatic hydrocarbons and hydrogen chloride are supplied to the fractionation means 35, in which they are divided into a lower boiling point aliphatic hydrocarbon stream containing hydrogen chloride and a higher boiling point aliphatic hydrocarbon stream which may contain some amount of the chlorides. The lower boiling point aliphatic hydrocarbon stream is passed to the fourth recovery zone 37 with an aqueous phase through the cooler 36 so that hydrogen chloride is recovered as hydrochloric acid and the liquified lower boiling point hydrocarbon is recovered. The cooler 36 is operated to cool the stream to a predetermined temperature. For example, when octene or lower aliphatic hydrocarbons are to be condensed, the temperature is preferably 120° C. or lower. The higher boiling point hydrocarbon containing the chloride may be returned to the heating chamber 32 so that it is subjected the catalytically cracking again.

When the organic phase recovered in the second recovery zone 9 is directly burnt off, harmful materials which contain chlorine are produced since the organic phase comprises the hydrocarbon chlorides. Thus, in the case of directly burning off is employed, any treatment apparatus which treats the harmful materials should be equipped.

To the contrary, when the conversion system 30 is provided, the chlorides are converted to the aliphatic hydrocarbons which can be used as, for example, a fuel. Even when the aliphatic hydrocarbons are to be burnt off, there is no need for the special apparatus for the treatment of the harmful chlorine-containing materials.

The catalyst contained in the vessel 35 comprises at least one of alumina catalyst or zeolite catalyst. It should be noted that the zeolite catalyst is higher cracking activity than that of the alumina catalyst so that it is likely to crack into lower hydrocarbons than the alumina catalyst, while alumina catalyst is resistant to hydrogen chloride. Considering this, a proper catalyst (including combination) should be selected depending on, for example, required hydrocarbons.

Alternatively, the heating chamber 32 may be eliminated and the organic phase from the vessel 31 may be directly supplied to the vessel 34 wherein the organic phase is gasified. Further, when the catalyst in the vessel 34 are to convert substantially all of the chlorides, the fractionation means may be eliminated.

EXAMPLES

In order to confirm the present invention, following Examples were carried out.

The Examples were performed by using a quartz glass tube reactor 16 as schematically shown in FIG. 3. The reactor contained 10 grams of ground polyvinyl chloride (PVC) particles 17 containing DOP as a plasticizer and nitrogen gas was supplied into the reactor through one end of thereof. The particles were heated and gasified at a temperature of around 300° C. over about 30 minutes, and a produced gas was analyzed using a gas chromatography.

Example 1

In the reactor, γ-alumina catalyst 18 (of which specific surface area was 300 m²/g) was placed. A center portion of the reactor 16 as the first recovery zone was kept at a temperature of about 80° C. on which a needle-like crystal 19 was obtained. Then, weights of the obtained crystal, a residue which was left in the reactor after thermal cracking and a gaseous stream recovered in a second recovery zone 20 were measured. The results are shown in FIG. 4A. As seen from FIG. 4A, 0.9 g of needle-like crystal phthalic anhydride was obtained. Namely, most of the plasticizer contained in the plastic material 17 were recovered.

Example 2

Example 1 was repeated except that synthesized zeolite catalyst (manufactured by Mobil Oil Corporation, trade name "H-ZSM-5" having a $SiO_2/Al_2O_3$ ratio of 70) was used in place of the γ-alumina catalyst. The results are shown in FIG. 4B. As seen from FIG. 4B, 1.0 g of phthalic anhydride needle-like crystal was obtained. Namely, substantially all of the plasticizer contained in the plastic material 17 were recovered.

Example 3

Example 1 was repeated except that no catalyst was used. The results are shown in FIG. 4C. As seen from FIG. 4C, 0.3 g of needle-like crystal phthalic anhydride was obtained. Namely, about 30% of the plasticizer originally contained in the plastic material 17 were recovered.

Example 4

Example 1 was repeated so many times to produce an aged catalyst due to the exposure to hydrogen chloride and finally the weights were measured. The results are shown in FIG. 4D. As seen from FIG. 4D, the recovery ratio of phthalic anhydride was reduced to 70%.

Example 5

Example 2 was repeated so many times to produce an aged catalyst due to the exposure to hydrogen chloride and finally the weights were measured. The results are shown in FIG. 4E. As seen from FIG. 4E, the recovery ratio of phthalic anhydride was reduced to 40%.

When considering the results of Examples 4 and 5, it is seen that each of the aged catalysts shows the reduction of the cracking activity, and that the cracking activity of the zeolite catalyst is more reduced than that of the alumina catalyst.

Further, there formed a liquid component 21 inside the reactor in Examples 3, 4 and 5 as seen from FIGS. 4C to 4E. To the contrary, there formed no liquid component, when non-aged catalyst was used.

Figure 5:
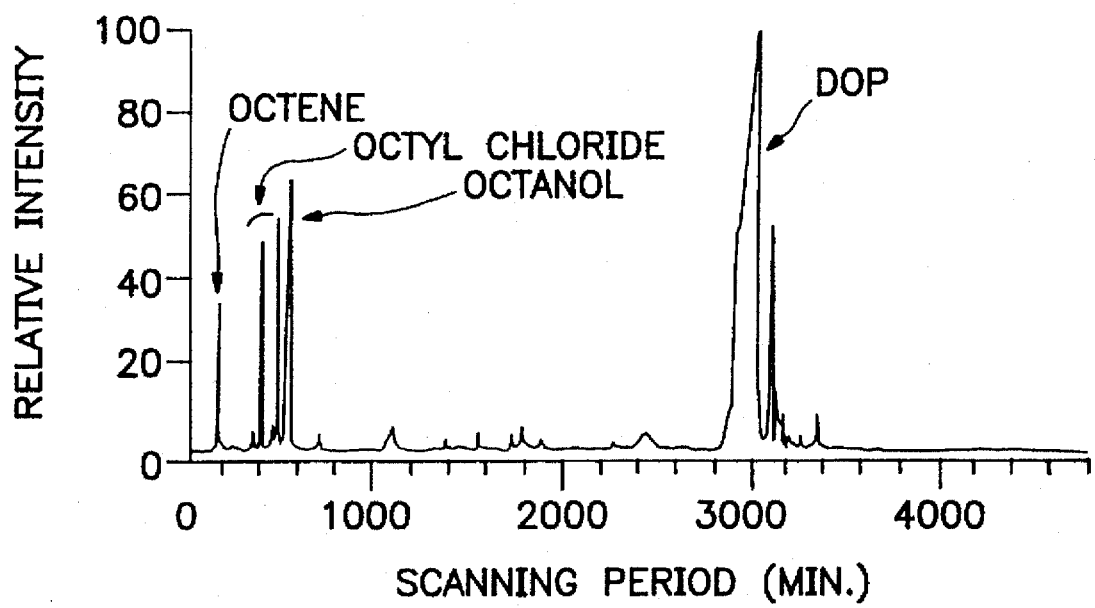
FIG. 5 is a gas chromatogram of a liquid component in Example 3 in which no catalyst was used.
Figure 6:
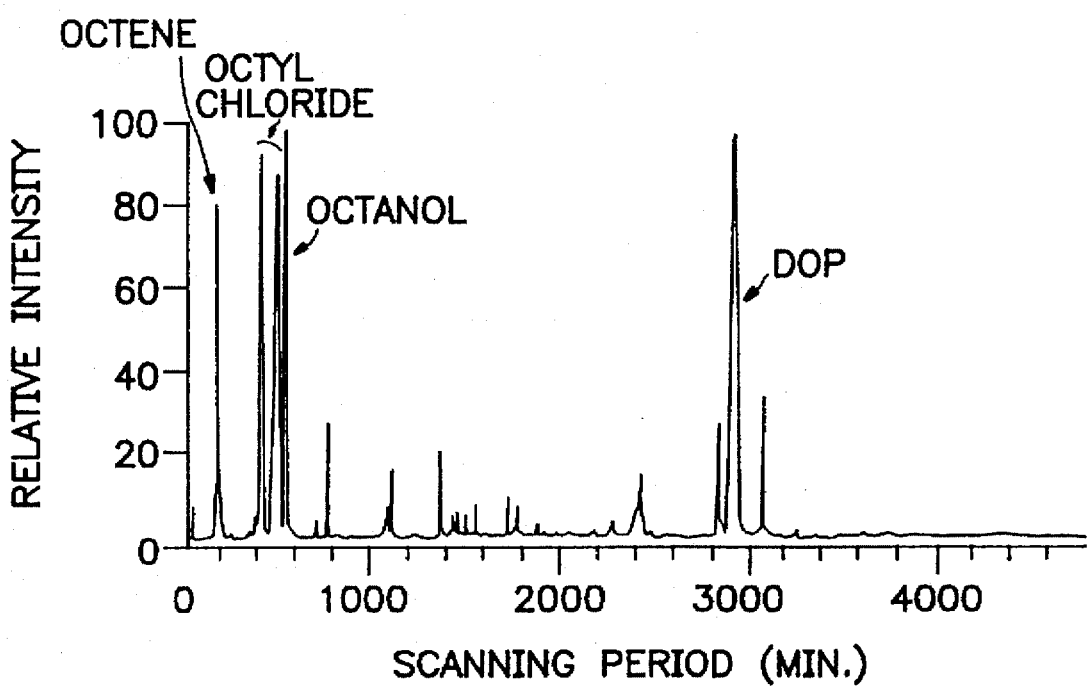
FIG. 6 is a gas chromatogram of a liquid component in Example 4 in which hydrogen chloride aged γ-alumina catalyst was used.
Figure 7:
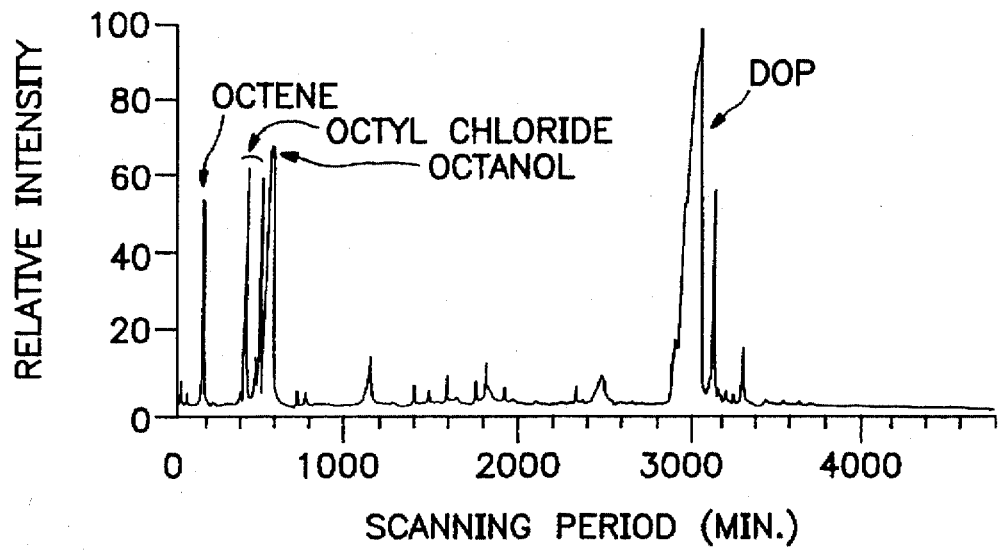
FIG. 7 is a gas chromatogram of a liquid component in Example 5 in which hydrogen chloride aged zeolite catalyst was used.
Figure 8:
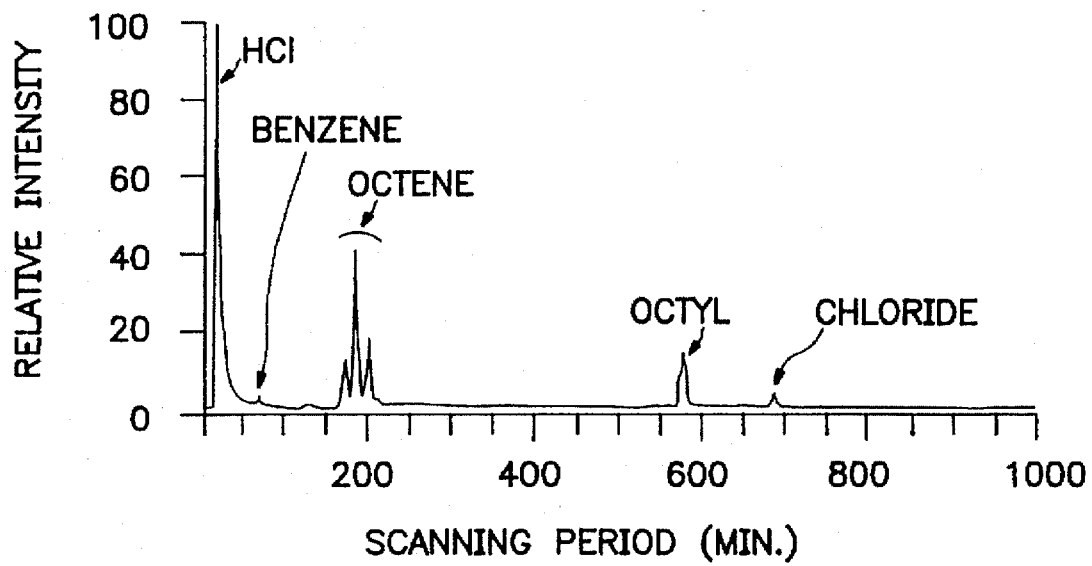
FIG. 8 is a gas chromatogram of a gaseous component in Example 1 in which γ-alumina catalyst was used.

When the liquid component was analyzed using the gas chromatography and the results are shown in FIGS. 5 to 7. It is seen from FIGS. 5 to 7 that the liquid component contains, in addition to octene, octyl chloride and octanol which were produced by the cracking of the plasticizer material, DOP which was not cracked and present intactly. In addition, it is seen that the aged γ-alumina catalyst left a less amount of phthalate relative to Examples 3 and 5.

In addition, the gas recovered in the recovery zone 20 was analyzed using the gas chromatography and the results thereof are shown in FIGS. 8 to 12. It is seen from these data that Example 1 which used γ-alumina catalyst 18 produced a large amount of lower boiling point hydrocarbons comprising octene.

Figure 9:
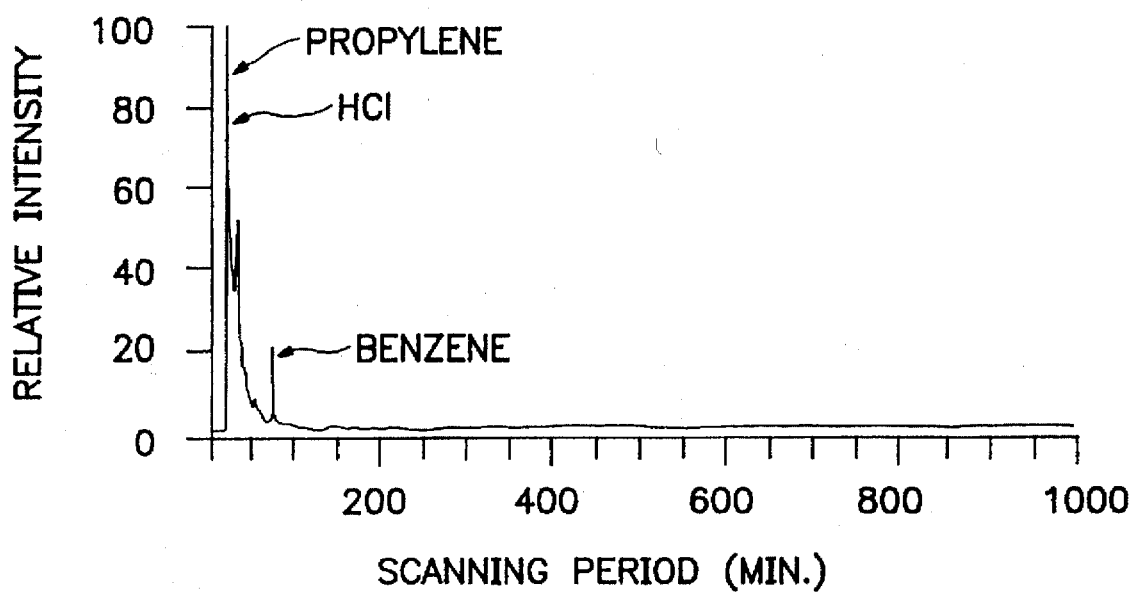
FIG. 9 is a gas chromatogram of a gaseous component in Example 2 in which zeolite catalyst was used.
Figure 10:
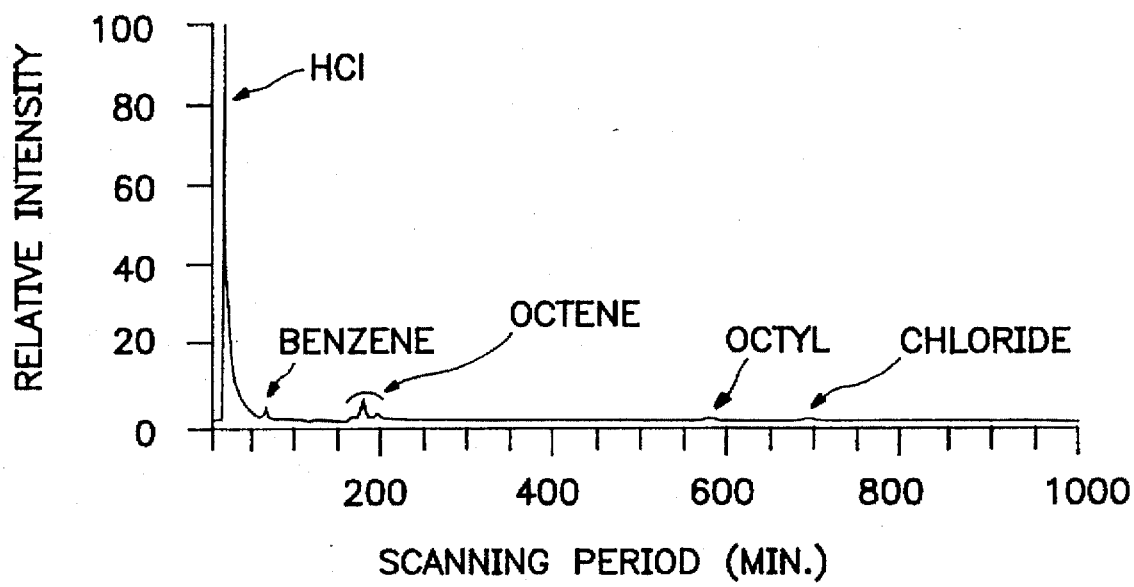
FIG. 10 is a gas chromatogram of a gaseous component in Example 3 in which no catalyst was used.
Figure 11:
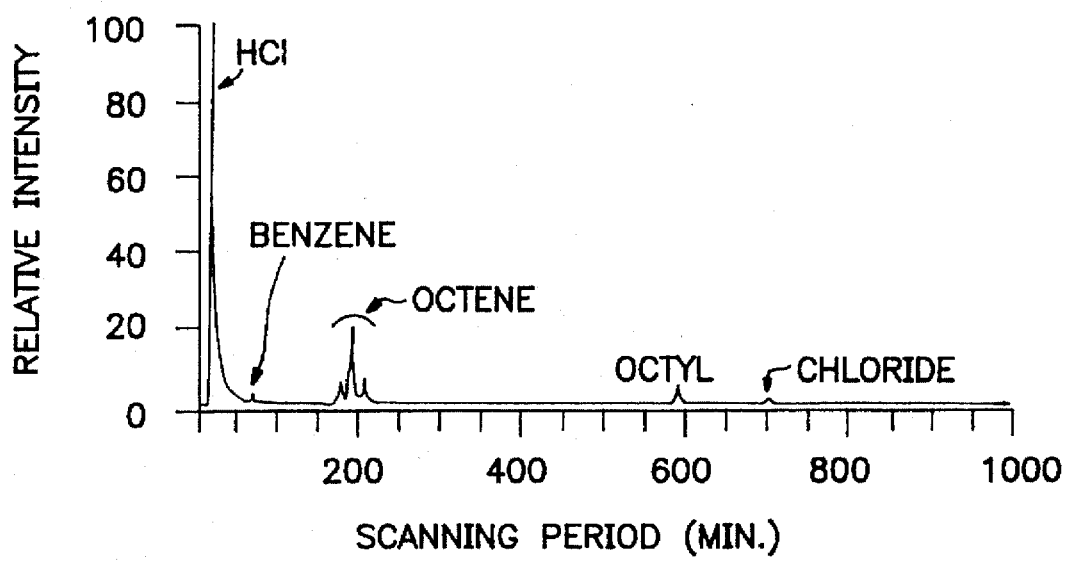
FIG. 11 is a gas chromatogram of a gaseous component in Example 4 in which hydrogen chloride aged γ-alumina catalyst was used.
Figure 12:
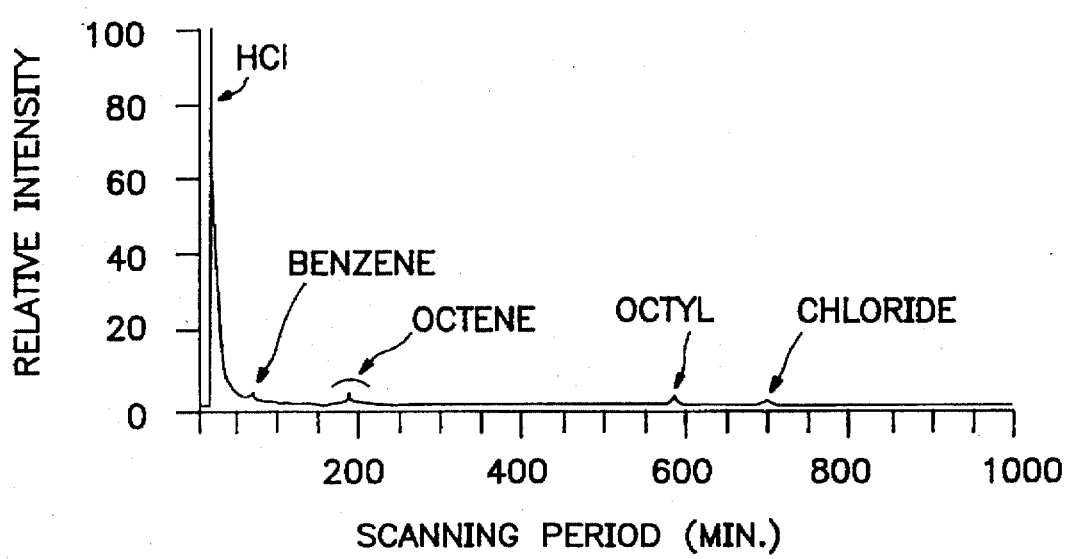
FIG. 12 is a gas chromatogram of a gaseous component in Example 5 in which hydrogen chloride aged zeolite catalyst was used.

In Example 2 using the zeolite catalyst 18, it is confirmed that a large amount of propylene was produced by cracking into a further lower molecular weight hydrocarbon as seen from FIG. 9. In Example 3 in which no catalyst was used and in Example 5 in which the zeolite catalyst aged by hydrogen chloride was used, it is confirmed that only a small amount of low molecular weight hydrocarbons was formed such as benzene and octene as seen from FIGS. 10 and 12.

In Example 4 in which the aged γ-alumina catalyst was used, although low molecular weight hydrocarbons such as octene were reduced to a certain extent compared with before the aging, an amount of the produced hydrocarbons are larger than that of Example 3 or 5.

Example 6

Figure 13:
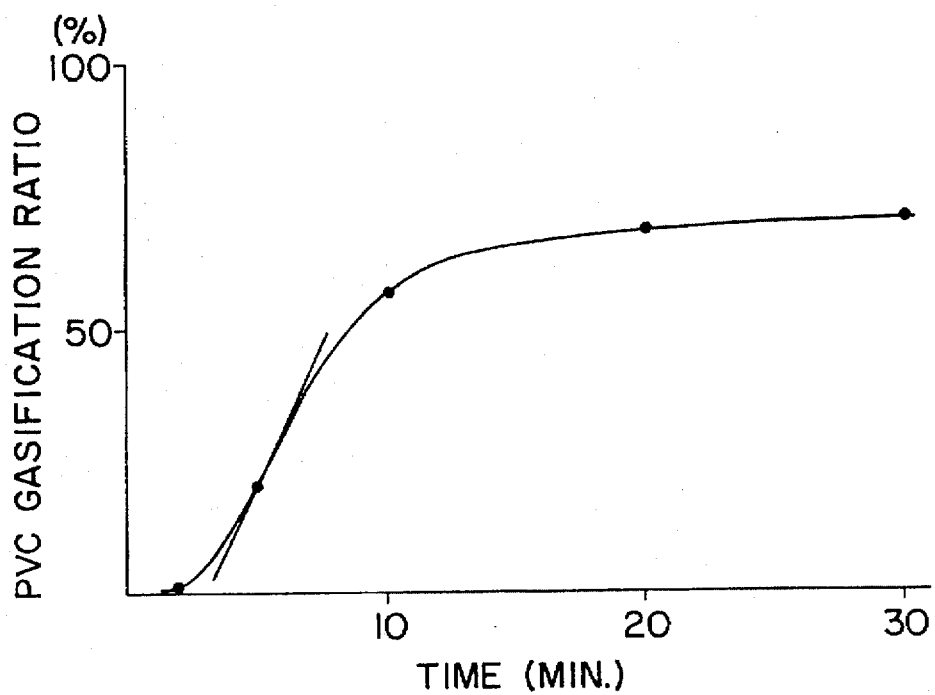
FIG. 13 is a graph which shows a relationship between a gasification rate of a polyvinyl chloride and a heating time in Example 6.

A gasification rate in the first heating chamber 1 of the first cracking zone 2 was measured by heating one gram of a polyvinyl chloride (PVC) at 300° C. over a varying period and determining a weight loss of PVC. The results are shown in FIG. 13. In the graph shown in FIG. 13, a maximum slope against of the curve was measured as a maximum gasification ratio which was about 0.1 g/min. Thus, it is confirmed that at least 10 minutes are required for the gasification of the plastic material.

Example 7

Figure 14:
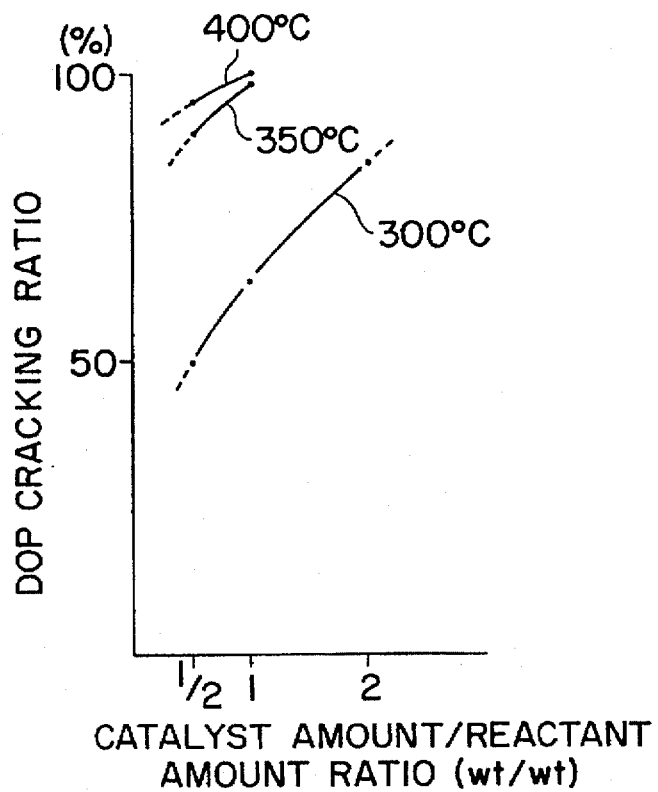
FIG. 14 is a graph which shows a relationship between a cracking ratio and a catalyst/plasticizer weight ratio in Example 7.

A cracking ratio in the first catalyst vessel 10 of the first cracking zone 2 was measured by passing vaporized DOP through the catalyst vessel at a predetermined weight ratio of the catalyst to DOP and analyzing a DOP content in a gas discharged from the catalyst vessel. The weight ratio (catalyst/DOP) was 0.5/1, 1/1 or 2/1 and a cracking temperature was 300° C., 350° C. or 400° C. The used catalyst was amorphous alumina (having a specific surface area of 200 $m^2/g$). The results are shown in FIG. 14. It is seen that the weight ratio of the catalyst to the plasticizer is preferably not lower than 1 and the cracking temperature is not lower than 350° C. for the purpose of more sufficient cracking.

Example 8

In this Example, the conversion of an aliphatic hydrocarbon chloride to hydrocarbons was studied so as to simulate the conversion system 30.

Figure 15:
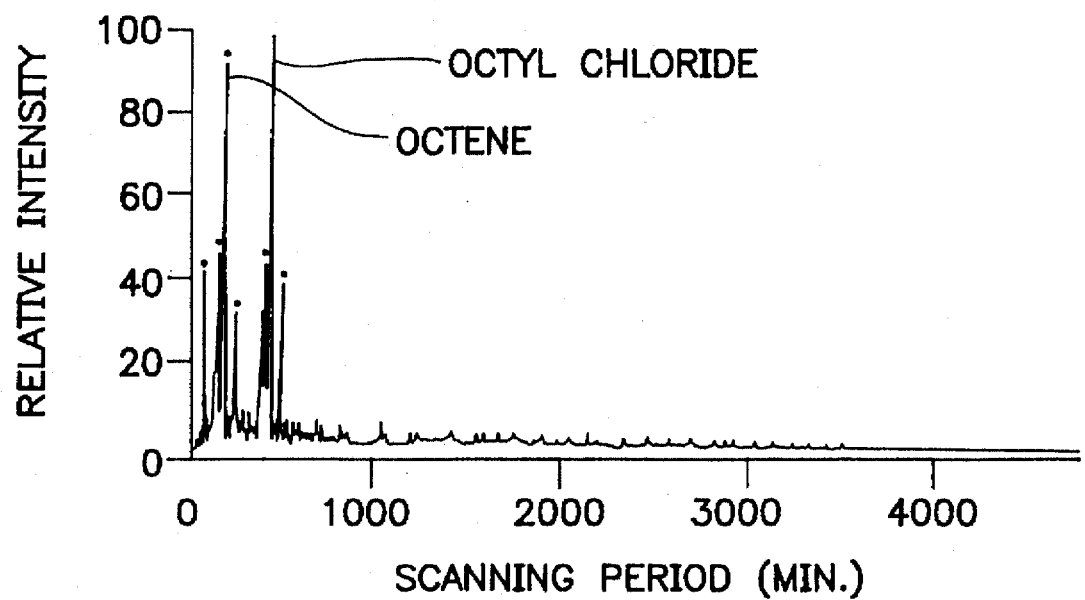
FIG. 15 is a gas chromatogram of a recovered hydrocarbon stream from the first cracking zone in the case of DOP in Example 8.
Figure 16:
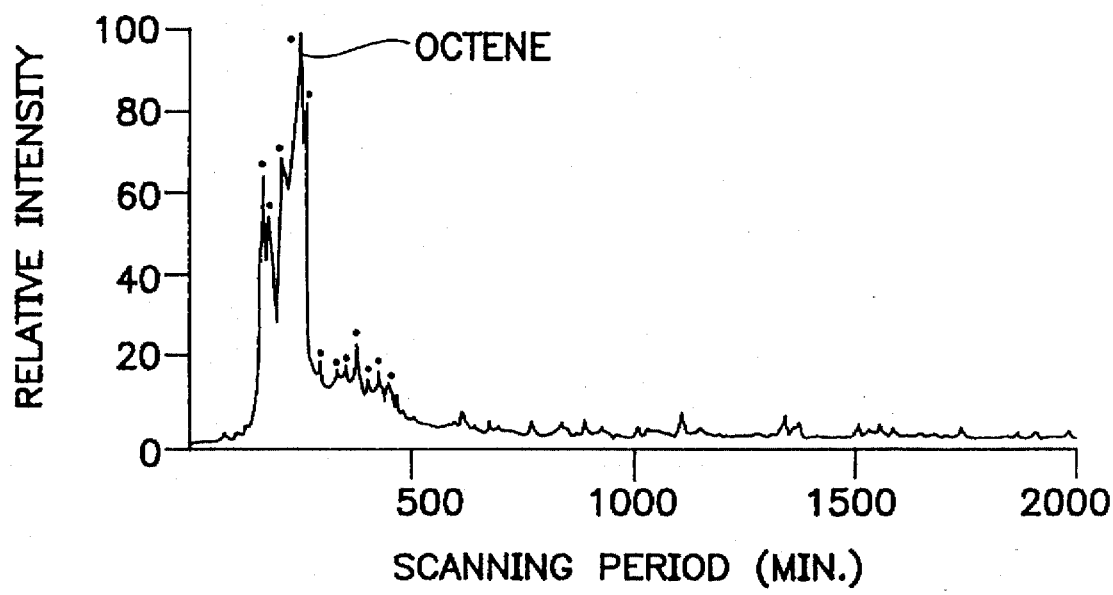
FIG. 16 is a gas chromatogram of a recovered hydrocarbon stream from the conversion system in the case of DOP in Example 8.

A polyvinyl chloride waste material containing DOP was cracked in the reactor of the first cracking system 2 to recover a hydrocarbon stream in the recovery zone 9, which was then converted in the conversion system 30. A produced stream discharged from the system 30 was analyzed. The results are shown in FIGS. 15 and 16. In this conversion, amorphous alumina (having a specific surface area of 300 $m^2/g$) was used.

FIG. 15 shows a gas chromatogram of the hydrocarbon stream recovered in the second recovery system 9. It is seen that the stream contains, in addition to the hydrocarbon such as octene, the hydrocarbon chlorides such as octyl chloride.

FIG. 16 shows a gas chromatogram of the stream discharged from the conversion system 30. It shows the absence of the chlorides in the hydrocarbons, which means that the chlorides present in the recovered stream was almost converted to the hydrocarbons in the conversion system 30.

Example 9

Figure 17:
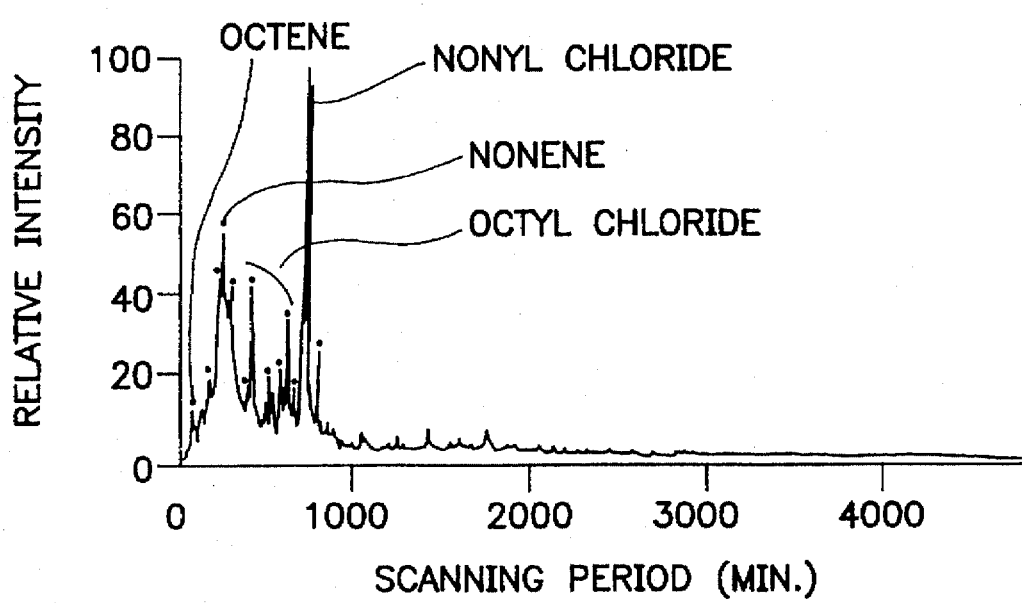
FIG. 17 is a gas chromatogram of a recovered hydrocarbon stream from the first cracking zone in the case of DNP in Example 9.
Figure 18:
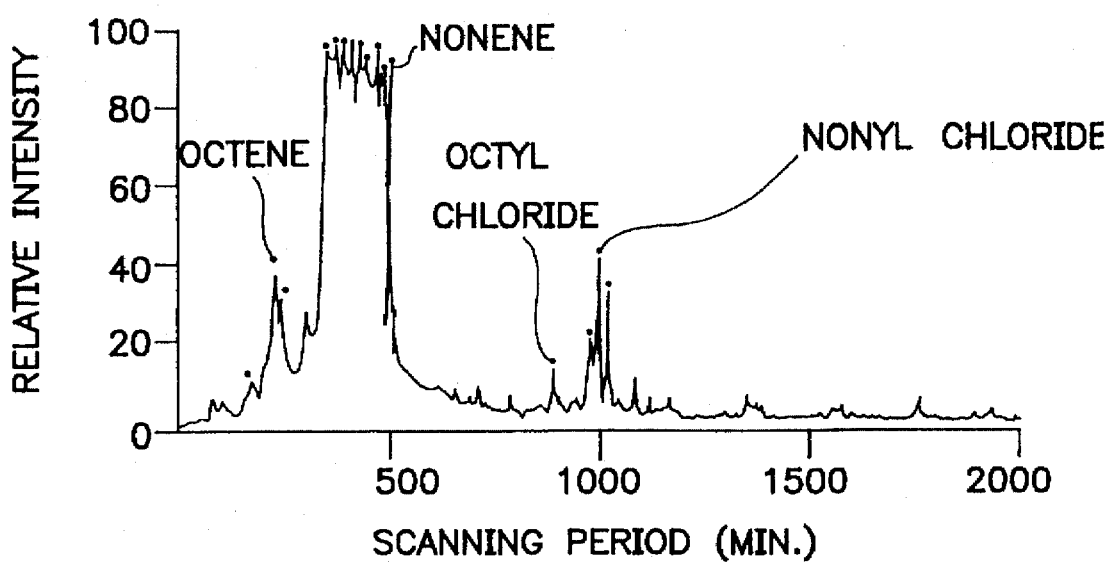
FIG. 18 is a gas chromatogram of a recovered hydrocarbon stream from the conversion system in the case of DNP in Example 9.

Example 8 was repeated by using another polyvinyl chloride containing DNP as the plastic material and results are shown in FIGS. 17 and 18.

FIG. 17 shows a gas chromatogram of the hydrocarbon stream recovered in the second recovery system 9. It is seen that the stream contains, in addition to the hydrocarbon such as octene and nonene, an large amount of the hydrocarbon chlorides such as octyl chloride and nonyl chloride.

FIG. 18 shows a gas chromatogram of the stream discharged from the conversion system 30. It shows that there remains a small amount of the chlorides in the hydrocarbons, which means that almost all of the chlorides present in the recovered stream was converted to the hydrocarbons in the conversion system 30.

The stream discharged from the catalyst vessel 34 may be then supplied to a fractionation means 34 in which the remaining chlorides in a small amount and higher hydrocarbons are recovered from a bottom of the means 34 and recovered stream is returned to the heating chamber 32 so that they are subjected to the conversion step again.

Example 10

Figure 19:
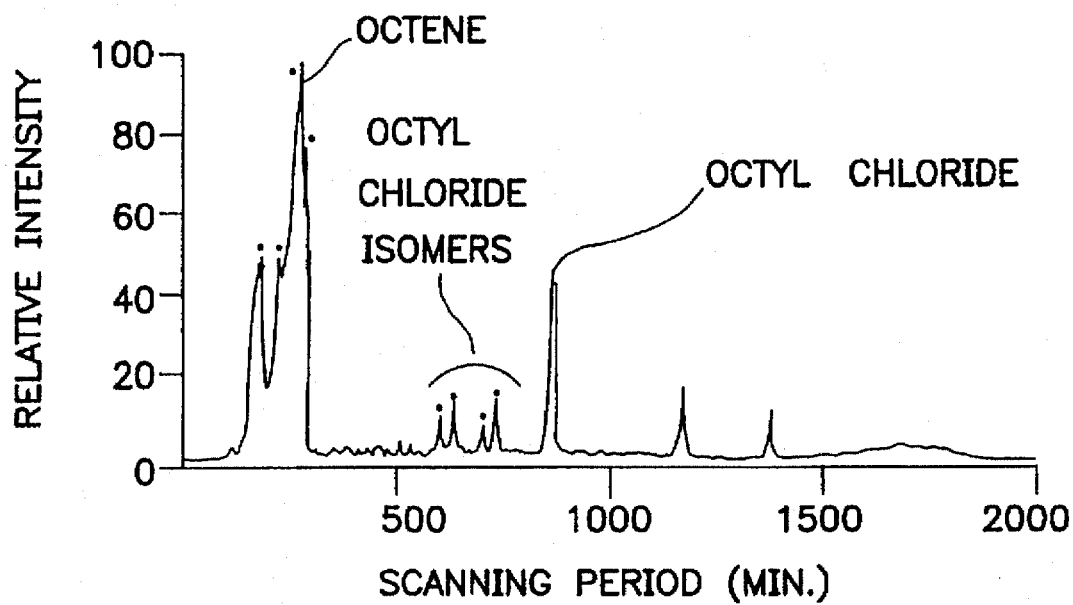
FIG. 19 is a gas chromatogram of a converted effluent from the conversion system in Example 10 using octyl chloride.

In order to further study the conversion step, octyl chloride was heated to a temperature of about 300° C. and passed through the catalyst vessel 34 containing amorphous alumina catalyst having a specific surface area of 300 $m^2/g$ and a oil component discharged from the vessel and liquefied was analyzed using the gas chromatography. The results are shown in FIG. 19. It is seen from FIG. 19 that most of octyl chloride was converted to octene and remaining amounts of octyl chlorides including isomers were extremely small.

Example 11

Figure 20:
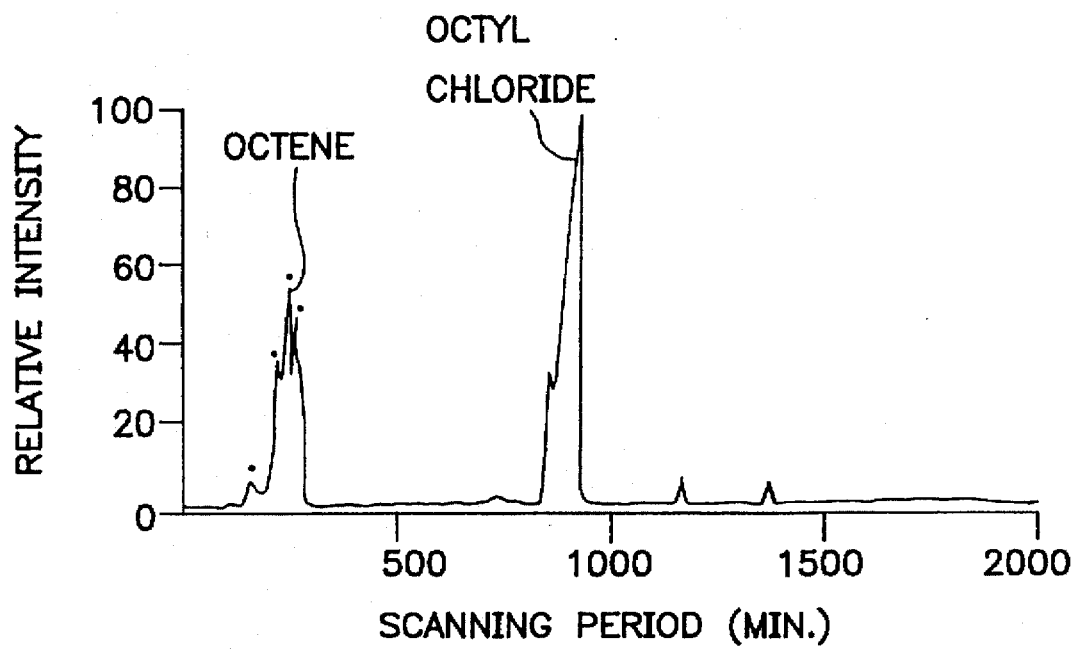
FIG. 20 is a gas chromatogram of a converted effluent from the conversion system in Example 11 using octyl chloride.

Example 10 was repeated except that alumina catalyst having a specific surface area of 200 $m^2/g$ was used in place of the alumina catalyst having a specific surface area of 300 $m^2/g$. The results are shown in FIG. 20. It is seen that from FIG. 20 that an amount of the remaining octyl chloride is larger than that of Example 10 but a fairly large amount of the supplied octyl chloride was converted to octenes.

Example 12

Figure 21:
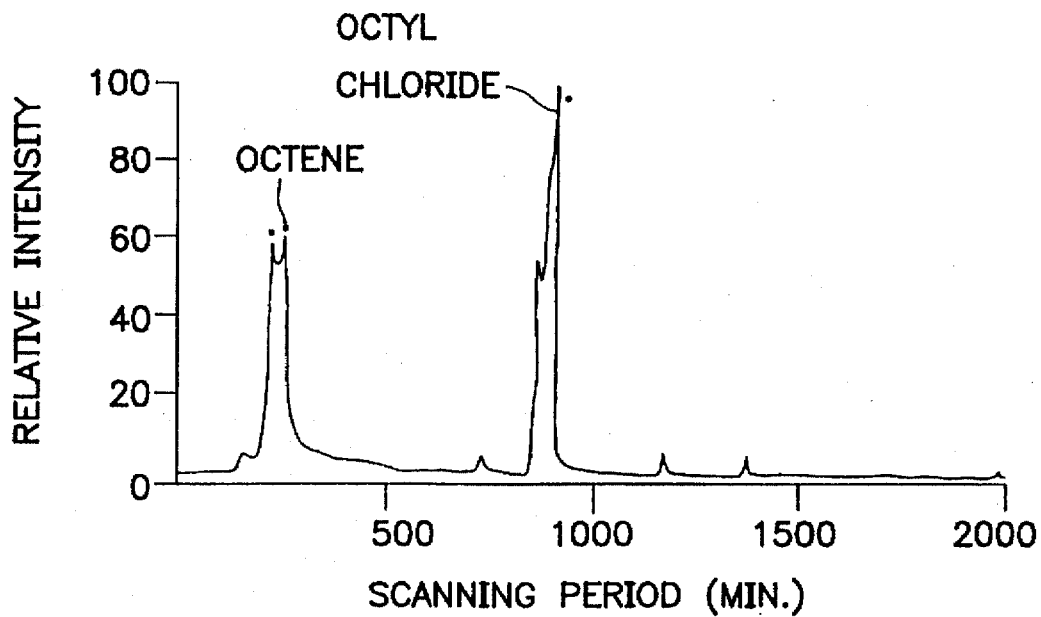
FIG. 21 is a gas chromatogram of a converted effluent from the conversion system in Example 12 using octyl chloride.

Example 10 was repeated except that alumina catalyst having a specific surface area of 140 $m^2/g$ was used in place of the alumina catalyst having a specific surface area of 300 $m^2/g$. The results are shown in FIG. 21. It is seen from FIG. 21 that an n amount of the remaining octyl chloride is more increased than that of Example 11 and a some amount of the supplied octyl chloride was converted to octenes.

Considering the results of Examples 10 to 12, it is seen that when the specific surface area of the solid acid catalyst is larger, a larger amount of octyl chloride is converted octenes, namely conversion efficiency is improved.

Example 13

Figure 22:
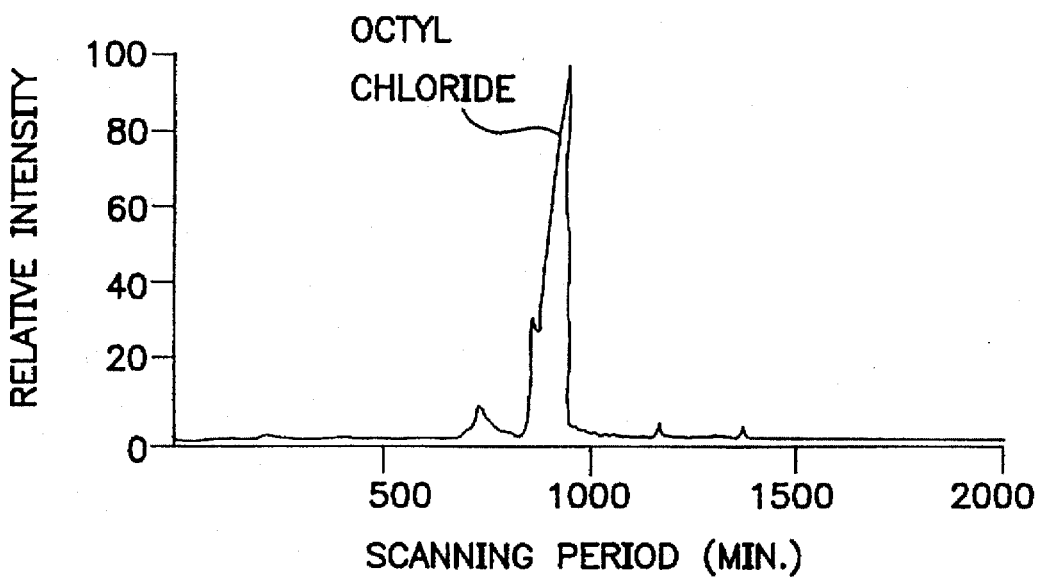
FIG. 22 is a gas chromatogram of a converted effluent from the conversion system in Example 13 using octyl chloride.

Example 10 was repeated except that no catalyst was used. The results are shown in FIG. 22. It is seen from FIG. 22 that almost no octyl chloride was converted to octene, which means that the conversion to the aliphatic hydrocarbons needs the use of the solid acid catalyst.

Example 14

A gasification rate of the hydrocarbon chlorides in the heating chamber 32 was measured by heating one gram of octyl chloride to a-temperature of 300° C. and measuring a weight loss of octyl chloride. The results are shown in FIG. 23 which shows the weight loss ratio versus a heating period.

Figure 23:
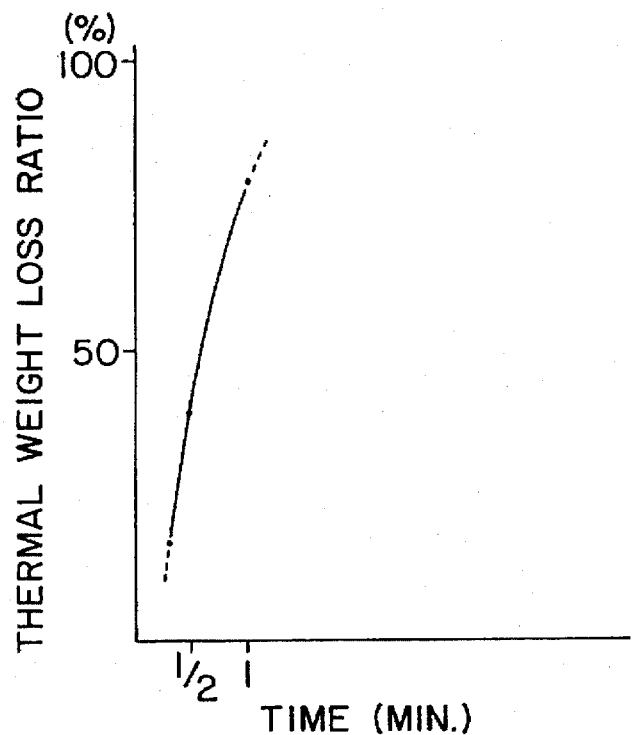
FIG. 23 is a graph which shows a relationship between a gasification rate of octyl chloride and a heating time in Example 14.

From the graph of FIG. 23, a maximum slope of the curve was estimated as the gasification ratio which was 0.1 g/min. Thus, it is expected that it takes at least 10 minutes to gasify all octyl chloride.

Example 15

The conversion of octyl chloride to octene was carried out with varying a weight of the catalyst relative to one gram of octyl chloride and a temperature to be heated and analyzing an effluent from the catalyst vessel using the gas chromatography.

Figure 24:
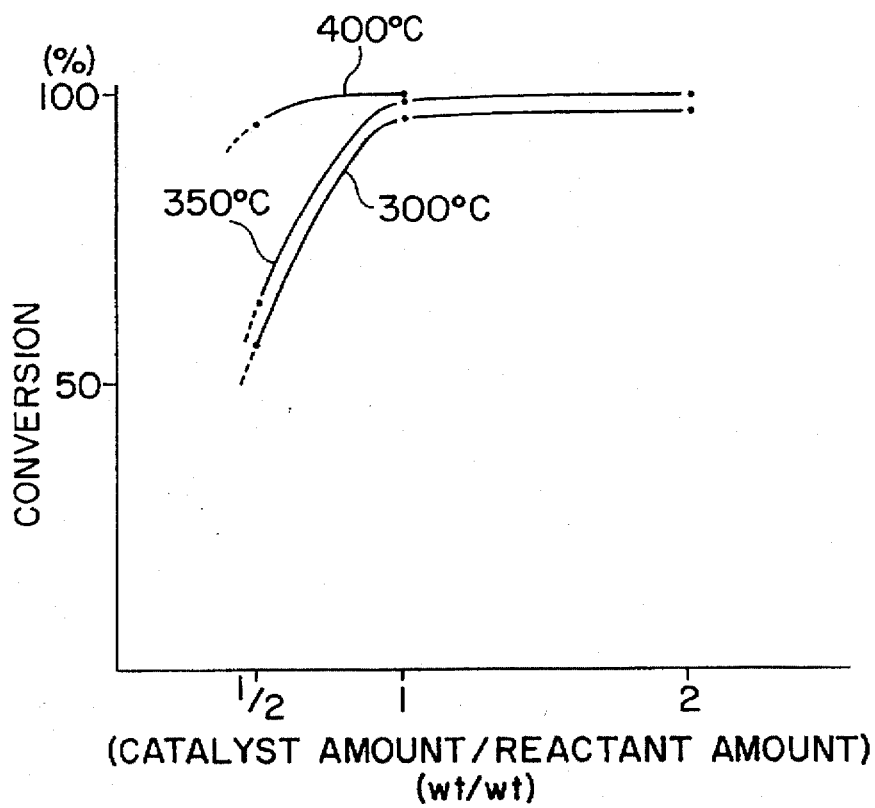
FIG. 24 is a graph which shows a relationship between a conversion and a catalyst/plasticizer weight ratio in Example 15.

The weight ratio of the catalyst to octyl chloride was 0.5/1, 1/1 or 2/1, and the temperature was 300° C., 350° C. or 400° C. The catalyst was amorphous alumina having a specific surface area of 200 $m^2/g$. The results are shown in FIG. 24 which shows a conversion versus the weight ratio.

It is seen that the weight ratio of the catalyst/octyl chloride is preferably not smaller than 1, and the temperature is preferably not lower than 300° C.

What is claimed is:

1. A process to recover phthalic anhydride from a plastic material which contains a plasticizer comprising a phthalate ester comprising the steps of:

(a) heating the plastic material so that the plastic material is gasified to produce a gaseous first product, (b) contacting the gaseous first product with alumina catalyst so that the gaseous first product is catalytically cracked to produce a first catalytically cracked product comprising phthalic anhydride; and (c) recovering phthalic anhydride from the first catalytically cracked product.

2. The process according to claim 1 wherein the plastic material comprises a chlorine containing plastic material and the process further comprises: (d) recovering hydrogen chloride after step (c) which is produced by the gasification in step (a).

3. The process according to claim 2 wherein the first catalytically cracked product comprises hydrocarbon chlorides and the process further comprises:

(e) gasifying hydrocarbon chlorides to provide gasified chlorides;

(f) converting the gasified chlorides to hydrogen chloride and hydrocarbons by catalytically cracking the chlorides in the presence of a solid acid catalyst so that a catalytically cracked product is produced; and (g) recovering the hydrocarbons from the catalytically cracked product of (f).

4. The process according to claim 1 wherein the process further comprises (h) heating a residue from the plastic material which is left after step (a) so that the residue is gasified to produce a second product, (i) contacting the second product with a solid acid catalyst so that the second product is catalytically cracked to produce a second catalytically cracked product comprising lower boiling point hydrocarbons; and (j) recovering the lower boiling point hydrocarbons from the second catalytically cracked product.

5. The process according to claim 2 wherein the process further comprises (h) heating a residue from the plastic material which is left after step (a) so that the residue is gasified to produce a second product, (i) contacting the second product with a solid acid catalyst so that the second product is catalytically cracked to produce a second catalytically cracked product comprising lower boiling point hydrocarbons; and (j) recovering the lower boiling point hydrocarbons from the second catalytically cracked product.

6. The process according to claim 3 wherein the process further comprises (h) heating a residue from the plastic material which is left after step (a) so that the residue is gasified to produce a second product, (i) contacting the second product with a solid acid catalyst so that the second product is catalytically cracked to produce a second catalytically cracked product comprising lower boiling point hydrocarbons; and (j) recovering the lower boiling point hydrocarbons from the second catalytically cracked product.

7. The process according to claim 4 wherein the solid acid catalyst is an alumina catalyst.

8. The process according to claim 5 wherein the solid acid catalyst is an alumina catalyst.

9. The process according to claim 6 wherein the solid acid catalyst of (i) is an alumina catalyst.

* * * * *